(12) United States Patent
Keller

(10) Patent No.: US 6,302,889 B1
(45) Date of Patent: Oct. 16, 2001

(54) SURGICAL CERCLAGE BAND

(75) Inventor: Arnold Keller, Kayhude (DE)

(73) Assignee: Waldemar Link (GmbH & Co.), Hamburg (DE)

( * ) Notice: Subject to any disclaimer, the term of this patent is extended or adjusted under 35 U.S.C. 154(b) by 0 days.

(21) Appl. No.: 09/666,190

(22) Filed: Sep. 21, 2000

(30) Foreign Application Priority Data

Sep. 24, 1999 (DE) .......................................... 299 16 884 U

(51) Int. Cl.[7] .................................................. A61B 17/56
(52) U.S. Cl. .............................................................. 606/74
(58) Field of Search ..................................... 606/1, 53, 60, 606/72, 74, 139, 151; 24/269, 20 TT

(56) References Cited

U.S. PATENT DOCUMENTS

| | | | |
|---|---|---|---|
| 1,874,731 | * | 8/1932 | Younce .................................. 24/269 |
| 3,962,759 | * | 6/1976 | Nagai ..................................... 24/269 |
| 4,388,748 | * | 6/1983 | Riedel .................................... 24/269 |
| 5,356,412 | * | 10/1994 | Gold et al. ............................. 606/74 |
| 5,356,417 | | 10/1994 | Golds . | |

FOREIGN PATENT DOCUMENTS

| | | |
|---|---|---|
| 27 30 571 A1 | 1/1978 | (DE) . |
| 35 38 645 A1 | 5/1987 | (DE) . |
| 197 18 903 A1 | 12/1997 | (DE) . |
| 94/26192 | 11/1994 | (WO) . |

* cited by examiner

*Primary Examiner*—Gene Mancene
*Assistant Examiner*—Eduardo C. Robert
(74) *Attorney, Agent, or Firm*—Morrison & Foerster LLP

(57) ABSTRACT

Disclosed is a device for securing a bone during surgery. The devices includes a band portion, a tightening buckle, and a tightening shaft. The band portion can be wrapped around a bone during surgery to secure the bone. The tightening buckle and tightening shaft are used to fasten the band portion. The tightening buckle has a wall with a tooth for engaging the tightening shaft.

5 Claims, 1 Drawing Sheet

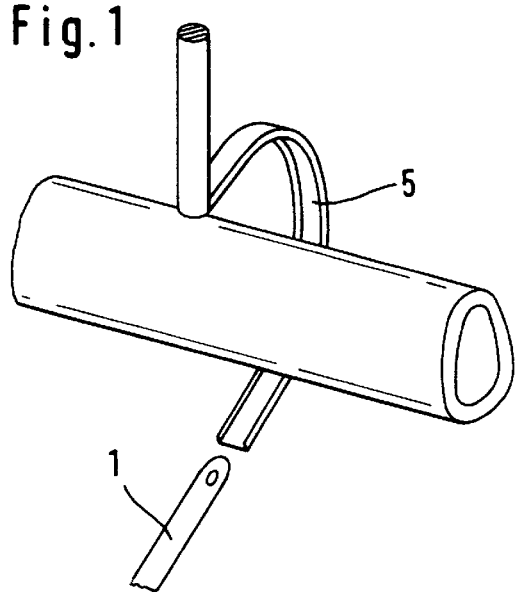
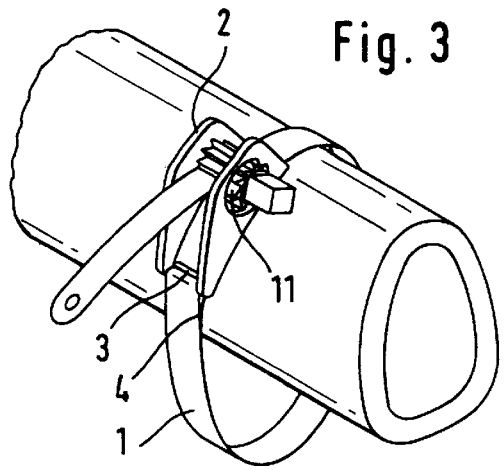
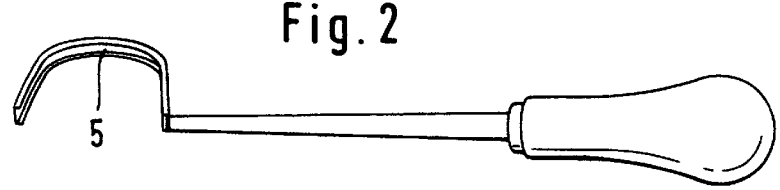
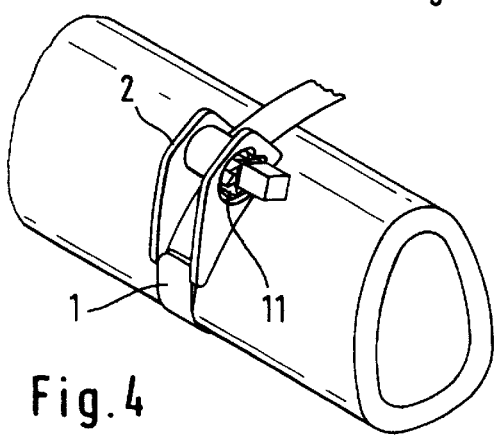
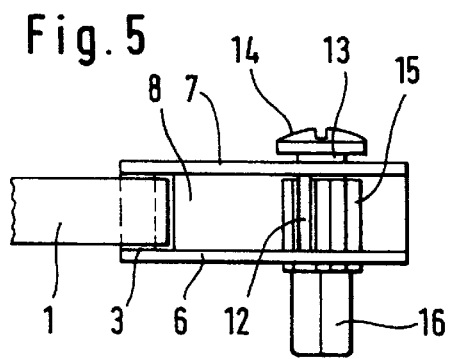
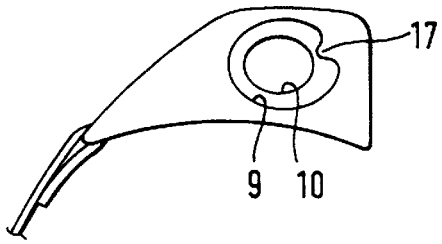
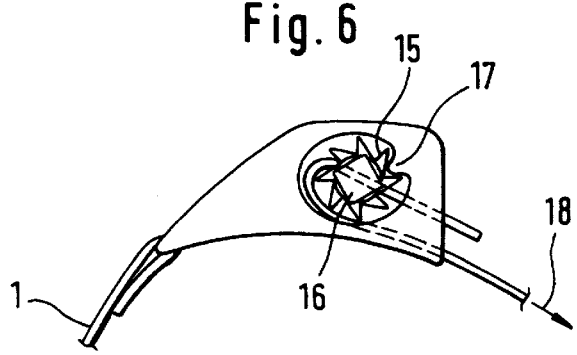

SURGICAL CERCLAGE BAND

TECHNICAL FIELD OF THE INVENTION

The present invention relates to a device for securing a bone during surgery. More particularly, this invention relates to a cerclage band that can securely bind a bone to prevent splintering of the bone during surgery.

BACKGROUND OF THE INVENTION

Cerclage bands are known (WO 9426192) in which a tightening buckle, which is connected to one end of a band part, has two side walls comprising openings which lie opposite one another and in which a tightening shaft is mounted which is intended for tightening the free end of the band.

Conventional hose clamps are known in which the openings for mounting the tightening shaft have a locking tooth and, in the area of the two openings, the tightening shaft has interacting teeth. A peg-shaped handling part protrudes from the tightening buckle on one side for engagement of a key.

SUMMARY OF THE INVENTION

This invention provides a cerclage band that can securely bind a bone to prevent splintering of the bone during surgery. In one embodiment, the cerclage band comprises a band part, a tightening buckle and a tightening shaft. The tightening buckle is connected to one end of the band part. The tightening buckle has a first side wall and a second side wall. The two side walls enclose a space for receiving a free end of the band part. The first side wall has a first opening having a locking tooth, and the second side wall has a second opening. The tightening shaft is mounted inside the first and second openings. The tightening shaft has toothing that can interact with the locking tooth of the first side wall while the tightening shaft is in a untoothed area of the second opening. The first opening is oblong so that the tightening shaft can be moved out of engagement with the locking tooth.

Preferably, the tightening shaft has a handling part. Preferably, the second opening is oblong shape. Preferably, the handling section is peg shaped and is arranged on the side of the first opening.

BRIEF DESCRIPTION OF THE DRAWINGS

The invention will be explained below in more detail with reference to the drawing which represents an advantageous illustrative embodiment, where:

FIG. 1 shows the cerclage band being guided round a bone by means of the instrument shown in FIG. 2, FIG. 2 shows a u-shaped guide, FIG. 3 shows the cerclage band looped round the bone, but not yet tightened, FIG. 4 shows the tightened cerclage band, FIGS. 5 and 6 show a plan view and a side view of the tightening buckle on a larger scale, and FIG. 7 shows the band buckle with the tightening shaft removed.

DETAILED DESCRIPTION OF THE PREFERRED EMBODIMENTS

To prevent splintering of a bone while performing surgery on it, or to hold a splintered bone together, it is provided with a so-called cerclage band. This is a binding for which wire is normally used.

The present invention is a cerclage band that is easier to handle and safer than conventional cerclage bands. The surgical cerclage band according to the invention differs from the prior art in that the winding shaft has teeth only in the area of one of the two openings; the shaft area interacting with the other opening is untoothed. This one-sided arrangement of the teeth has the advantage that the band can be released again relatively easily by turning back the winding shaft. A precondition for this turning back is the release of the shaft teeth from the locking tooth of the opening. This is achieved by the winding shaft being pulled back from the locking tooth on the side in question. it would not be easy, in a small and inaccessible operating site, to draw back the other end of the shaft too, as would be readily possible in other technical fields, for example in hose clamps.

The tightening band is advantageously assigned a guiding instrument which has a U-shaped, rigid part which is guided around the part of the bone to be bound and which has a guide allowing the band part of the cerclage band to be guided more easily around the bone.

The cerclage band consists of the band part 1 and of the tightening buckle generally designated by the reference number 2, which buckle is connected at one end 3 to one end of the band part 1. The tightening band is made of metal or of a tension-proof synthetic and has sufficient strength to be able to exert the desired annular tension on the bone, and sufficient flexibility to be wound up or at least bent in the tightening buckle. For connecting the band part 1 to the tightening buckle 2, it is sufficient, in the case of a metal band, to guide the end 4 of the tightening band through a slit in the band buckle and to bend this back on the underside of the tightening band.

When it is to be used, the band part 1 is guided round the bone. To do this, it is expedient to use the instrument which is represented in FIGS. 1 and 2 and which has a U-shaped, essentially rigid guide through which the band part can be guided round the bone.

The band buckle is an essentially U-shaped bent metal sheet with two side walls 6, 7 on either side of a base part 8 connecting them. The clear space between the side walls 6, 7 is slightly greater than the width of the band part 1.

One side wall 6 comprises a first opening 9, the second side wall 7 comprises a slightly smaller opening 10 which is essentially flush with the opening 9. Both openings are oblong, the longitudinal direction corresponding approximately to the direction of tightening. They are intended to receive a winding shaft 11 which has a slit 12 through which the free end of the band part 1 is inserted before it is tightened. The winding shaft has an essentially cylindrical section 13 which lies in the second opening 10 and is secured therein by a head 14 which can be formed, for example, by a screw. Adjoining the section 13 there is are teeth 15 which take up essentially the whole length of the winding shaft 11 between the side walls 6, 7 and also the area which lies in the first opening 9 of the side wall 6. Extending outside the band buckle housing 6, 7, 8 is the peg-shaped handling section 16 of the winding shaft, which handling section has a square shape so that it can be operated by a key (not shown).

The first opening 9 in the side wall 6, in which the teeth 15 lie, comprises a locking tooth 17 at that end of the opening 9 which faces the end of the band buckle 2 receiving the free end of the band part 1. As can be seen in FIG. 6, the teeth of the winding shaft are held in engagement with this locking tooth by the band traction acting in the arrow direction. This prevents the winding shaft from turning back under the band traction. However, on account of their sawtooth shape, the teeth can move past the locking tooth 17 upon the tightening turning of the winding shaft, the winding shaft moving towards the left in FIG. 6.

After the band part 1 has been guided round the bone, its free end is inserted through the slit 12 of the winding shaft (FIG. 3) and drawn taut round the bone by forceps. Thereafter, one uses a key to begin turning the winding shaft in the clockwise direction (FIG. 6) until the necessary band tensioning is achieved. Any protruding end of the band part 1 causing interference can be cut off beforehand or afterwards.

If the cerclage band is to be removed again without cutting through it, the band part 1 is released from the tightening buckle 2. For this purpose, the winding shaft 11 has to be turned back. This is achieved by drawing the shaft back from the locking tooth 17 counter to the arrow direction 18 during the turning back operation. The oblong shape of the openings 9, 10 permits this movement of the winding shaft. The reverse movement of the winding shaft is therefore possible because the handling section 16 is directly adjacent to the opening 9 which comprises the locking tooth 17 and the toothed shaft section 15. It may also be sufficient to pivot the winding shaft about its section 13; in some cases the opening 10 does not therefore have to be of oblong design. In any event, a tool is engaged on the handling section 16, with which tool the shaft 11 is pulled back from the locking tooth 17 and turned back until the free end of the band part 1 can be withdrawn from the tightening buckle.

What is claimed is:

1. A surgical cerclage band, comprising:
   a band part;
   a tightening buckle connected to an end of the band part, wherein the tightening buckle has a first side wall and a second side wall, the first and second side walls enclosing a space for receiving another end of the band part, the first side wall having a first opening having a locking tooth, and the second side wall having a second opening; and
   a tightening shaft mounted inside the first opening and the second opening, wherein the tightening shaft has teeth that are configured to interact with the locking tooth of the first side wall while the tightening shaft is in an untoothed area of the second opening and wherein the first opening has an oblong shape so that the tightening shaft can be moved out of engagement with the locking tooth and wherein the tightening shaft has a handling part.

2. The cerclage band of claim 1, wherein the handling part comprises a free-standing handling section.

3. The cerclage band of claim 1, wherein the second opening has a oblong shape.

4. The cerclage band of claim 1, 2, or 3, wherein the handling section is peg shaped and is arranged on a side of the first opening.

5. The cerclage band of claim 1, 2, or 3, further comprising a U-shaped guide for guiding the band part around a bone.

* * * * *